US011492338B2

United States Patent
Eady et al.

(10) Patent No.: US 11,492,338 B2
(45) Date of Patent: Nov. 8, 2022

(54) FURAN SURFACTANT COMPOSITIONS AND METHODS

(71) Applicant: SIRONIX RENEWABLES, INC., Seattle, WA (US)

(72) Inventors: Shawn Eady, Seattle, WA (US); Sabrina Conrad, Seattle, WA (US); Trenton Wilke, Seattle, WA (US); Christoph Krumm, Seattle, WA (US)

(73) Assignee: SIRONIX RENEWABLES, INC., Seattle, WA (US)

( * ) Notice: Subject to any disclaimer, the term of this patent is extended or adjusted under 35 U.S.C. 154(b) by 0 days.

(21) Appl. No.: 17/599,029

(22) PCT Filed: May 3, 2021

(86) PCT No.: PCT/US2021/030410
§ 371 (c)(1),
(2) Date: Sep. 28, 2021

(87) PCT Pub. No.: WO2021/225932
PCT Pub. Date: Nov. 11, 2021

(65) Prior Publication Data
US 2022/0204467 A1   Jun. 30, 2022

Related U.S. Application Data

(60) Provisional application No. 63/019,485, filed on May 4, 2020.

(51) Int. Cl.
*C07D 307/64* (2006.01)
(52) U.S. Cl.
CPC .................................. *C07D 307/64* (2013.01)
(58) Field of Classification Search
None
See application file for complete search history.

(56) References Cited

U.S. PATENT DOCUMENTS

| | | | |
|---|---|---|---|
| 2,411,567 | A | 11/1946 | Wotherspoon |
| 4,443,559 | A | 4/1984 | Smith, Jr. |
| 4,477,382 | A | 10/1984 | Goel et al. |
| 5,338,517 | A | 8/1994 | Evans et al. |
| 5,387,705 | A | 2/1995 | Stipp et al. |
| 5,776,320 | A | 7/1998 | Marion et al. |
| 6,149,879 | A | 11/2000 | Forestiere et al. |
| 6,416,659 | B1 | 7/2002 | Groten et al. |
| 2004/0260137 | A1 | 12/2004 | Elomari et al. |
| 2014/0135359 | A1 | 5/2014 | Martineau |
| 2015/0150768 | A1 | 6/2015 | West et al. |
| 2015/0166596 | A1 | 6/2015 | Hill |
| 2016/0304479 | A1 | 10/2016 | Stensrud |
| 2017/0226075 | A1 | 8/2017 | Stensrud et al. |
| 2018/0051113 | A1 | 2/2018 | Yang et al. |

FOREIGN PATENT DOCUMENTS

| | | |
|---|---|---|
| CN | 104162447 B | 11/2017 |
| WO | 9627580 A1 | 9/1996 |
| WO | 2017079718 A1 | 5/2017 |
| WO | 2017079719 A1 | 5/2017 |
| WO | 2019040389 A1 | 2/2019 |
| WO | 2020227097 A1 | 11/2020 |

OTHER PUBLICATIONS

Corma, A., Iborra, S., & Velty, A. (2007). Chemical routes for the transformation of biomass into chemicals. Chemical reviews, 107(6), 2411-2502.
Ackman et al., "Ozonolysis of Unsaturated Fatty Acids I. Ozonolysis of Oleic Acid," Canadian Journal of Chemistry, vol. 39, No. 10, 1961, pp. 1956-1963.
Almqvist, "Furans from biomass: Production, applications and techno economic potential," Processum, Apr. 20, 2018, 9 pages.
Ben-Daniel et al., "Selective Aerobic Oxidation of Alcohols with a Combination of a Polyoxometalate and Nitroxyl Radical as Catalysts," Journal of Organic Chemistry, vol. 66, No. 25, Nov. 2001, pp. 8650-8653.
Bidange et al., "Ethenolysis: A Green Catalytic Tool to Cleave Carbon-Carbon Double Bonds," Chemistry A European Journal, vol. 22, No. 35, Aug. 22, 2016, pp. 12226-12244.
Xu et al., "Trialkylphosphine-Mediated Synthesis of 2-Acyl Furans from Ynenones," Organic Letters, vol. 19, Jun. 27, 2017, pp. 3556-3559.
Brown et al., "The Condensation of Furan and Sylvan with Some Carbonyl Compounds," Canadian Journal of Chemistry, vol. 34, No. 9, Sep. 1956, pp. 1147-1153.
Byrne et al., "Tools and techniques for solvent selection: green solvent selection guides," Sustainable Chemical Processes, vol. 4, No. 7, 2016, 24 pages.
Corberan et al., "Green oxidation of fatty alcohols: Challenges and opportunities," Applied Catalysis A: General, vol. 474, Mar. 2014, pp. 211-223.
Yow et al., "Hydrolysis of palm olein catalyzed by solid heteropolyacids," Journal of the American Oil Chemists' Society, vol. 79, 2002, pp. 357-361.
Engel et al., "Thermoreversible reactions on inorganic nanoparticle surfaces: Diels-Alder reactions on sterically crowded surfaces," Chemistry of Materials, vol. 25, Dec. 12, 2012, pp. 149-157.

(Continued)

*Primary Examiner* — Samantha L Shterengarts
(74) *Attorney, Agent, or Firm* — Fredrikson & Byron, P.A.

(57) ABSTRACT

Chemical compositions, and related methods for synthesizing furan, such as oleo-furan, surfactants, include calcium, magnesium, ammonium and/or lithium cations and one of a number of furan derivatives. Methods for synthesizing such furan surfactants containing calcium, magnesium, ammonium and/or lithium cations can include chemical reagents and purification procedures to prepare furan surfactants containing calcium, magnesium, ammonium and/or lithium cations. These furan surfactant compositions can be free of dioxane and ethoxylate.

20 Claims, 1 Drawing Sheet

(56) References Cited

OTHER PUBLICATIONS

Froidevaux et al, "Study of the Diels-Alder and retro-Diels-Alder reaction between furan derivatives and maleimide for the creation of new materials," RSC Advances, vol. 5, 2015, pp. 37742-37754, Abstract Only.

Gandini, "The furan/maleimide Diels-Alder reaction: A versatile click-unclick tool in macromolecular synthesis," Progress in Polymer Science, vol. 38, No. 1, Jan. 2013, pp. 1-29, Abstract Only.

Gheneim et al., "Diels-Alder reactions with novel polymeric dienes and dienophiles: synthesis of reversibly cross-linked elastomers," Macromolecules, vol. 35, No. 19, Aug. 8, 2002, pp. 7246-7253, Abstract Only.

Hong et al., "Selective oxidation of octadecan-1-ol to octadecanoic acid over $Co_3O_4/SiO_2$ catalysts," Reaction Kinetics and Catalysis Letters, vol. 81, Jan. 2004, pp. 13-20.

International Patent Application No. PCT/US2021/030410, International Search Report and Written Opinion dated Aug. 12, 2021, 11 pages.

Iovel et al., "Hydroxymethylation of Furan and its Derivatives in the Presence of Cation-Exchange Resins," Journal of Molecular Catalysis, vol. 57, No. 1, 1989, pp. 91-103.

Joseph, "Tunable Synthesis and Characterization of Oleo-Furan Sulfonate Surfactants from Renewable Furan and Fatty Acids," Dissertation submitted to the Faculty of University of Minnesota, May 2018, pp. 1-154.

Kadesch, "Ozonolysis of Fatty Acids and Their Derivatives," Progress in the Chemistry of Fats and other Lipids vol. 6, 1963, pp. 291-312.

Kan et al., "Catalytic oxidation of α-eicosanol into eicosanic acid in the presence of Ti-MCM-41 or active component supported Ti-MCM-41 catalysts," Microporous and Mesoporous Materials, vol. 44-45, Apr. 2001, pp. 609-617.

Liang et al., "Acid-Catalyzed Ring Opening of Furan in Aqueous Solution," Energy Fuels, vol. 32, No. 4, 2018, pp. 4139-4148.

Liu et al., "Molybdenum Oxide-Modified Iridium Catalysts for Selective Production of Renewable Oils for Jet and Diesel Fuels and Lubricants," ACS Catalysis, vol. 9, Jul. 16, 2019, pp. 7679-7689.

Lundin et al., "Intensified and Safe Ozonolysis of Fatty Acid Methyl Esters in Liquid $CO_2$ in a Continuous Reactor," AlChE Journal, vol. 63, No. 7, 2017, pp. 2819-2826.

Naik et al., "Liquid phase acylation of 2-methylfuran with fatty acid anhydride," NAM 26, 2019 North American Catalysis Society Meeting, Jun. 26, 2019, 3 pages.

Park et al., "Tunable Oleo-Furan Surfactants by Acylation of Renewable Furans," ACS Central Science, vol. 2, Issue 11, Oct. 19, 2016, pp. 820-824.

Pubchem. CID 54467179, Retrieved from the Internet <https://pubchem.ncbi.nlm.nih.gov/compound/54467179>, Dec. 4, 2011, pp. 1-6.

Pubchem. CID 68119, Retrieved from the Internet <https://pubchem.ncbi.nlm.nih.gov/compound/68119>, Mar. 26, 2005, pp. 1-19.

Pubchem, Compound Summary for SID 150925859, Modify Date: Jun. 3, 2019 [retrieved on Apr. 13, 2021]. Retrieved from the Internet: <URL: https://pubchem.ncbi.nlm.nih.gov/substance/150925859>, 7 pages.

Pubmed Compound Record for CID 14421037, '2-Ethyl-5-hexylfuran-3-sulfonic acid', U.S. National Library of Medicine, Feb. 9, 2007, retrieved from https://pubchem.ncbi.nlm.nih.gov/compound/14421037, 10 pages.

Pubmed Compound Record for CID 13090063, '4-Sulfo-5-methylfuran-2-carboxylic acid', U.S. National Library of Medicine, Feb. 8, 2007, pp. 1-10 (https://pubchem.ncbi.nlm.nih.gov/compound/13090063).

Pubmed Compound Record for CID 75388835, 'Methyl 4-[(3,5-dimethylphenoxy)sulfonyl]-5-methylfuran-2-carboxylate', U.S. National Library of Medicine, Jul. 12, 2014, pp. 1-9 (https://pubchem.ncbi.nlm.nih.gov/compound/75388835).

Saedi et al., "MIL-101 metal-organic framework: A highly efficient heterogeneous catalyst for oxidative cleavage of alkenes with $H_2O_2$," Catalysis Communications, vol. 17, Jan. 5, 2012, pp. 18-22.

Saha et al., "Advances in 5-hydroxymethylfurfural production from biomass in biphasic solvents," Green Chemistry, vol. 16, 2014, pp. 24-38.

Sakuth et al., "Reactive Distillation," Ullmann's Encyclopedia of Industrial Chemistry, Jan. 1, 2012, Wiley-VCH, Weinheim, pp. 263-276.

Shi et al., "Au—Pd nanoparticles on layered double hydroxide: Highly active catalyst for aerobic oxidation of alcohols in aqueous phase," Catalysis Communications, vol. 18, Feb. 2002, pp. 142-146.

Travis et al., "Osmium Tetroxide-Promoted Catalytic Oxidative Cleavage of Olefins: An Organometallic Ozonolysis," Journal of the American Chemical Society, vol. 124, No. 9, 2002, pp. 3824-3825.

Trubyanov et al., "High-pressure distillation: Simultaneous impact of pressure, temperature and loading on separation performance during distillation of high-purity gases in high-performance randomly-packed columns," Separation and Purification Technology, vol. 135, Oct. 2014, pp. 117-126.

Vauthier et al., "Interfacial Diels-Alder reaction between furan-functionalized polymer coatings and maleimide-terminated poly-(ethylene glycol)," The Journal of Physical Chemistry C, vol. 123, Jan. 22, 2019, pp. 4125-4132.

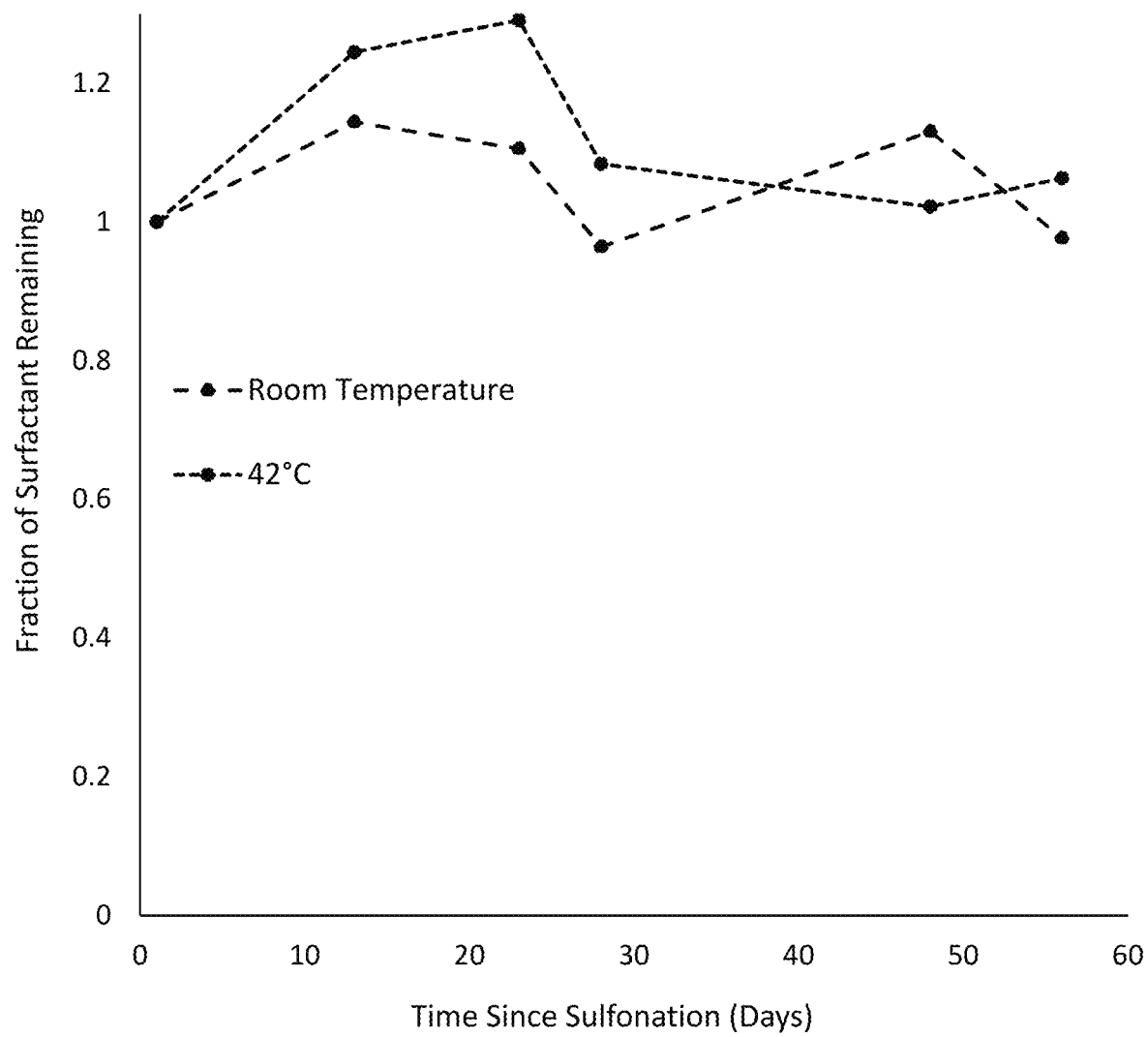

FURAN SURFACTANT COMPOSITIONS AND METHODS

RELATED APPLICATION

This application is a National Phase filing from International Patent Application No. PCT/US2021/030410, filed May 3, 2021, which claims priority to, and the benefit of, U.S. provisional patent application No. 63/019,485, filed May 4, 2020.

TECHNICAL FIELD

This disclosure generally relates to surfactant compositions and related methods for synthesizing such surfactants. In particular, disclosed herein are embodiments including dioxane-free furan surfactant compositions and related methods for synthesizing dioxane-free furan surfactants.

BACKGROUND

Surfactants are chemical compounds that have a variety of applications. Such applications can include household cleaners and detergents, institutional & industrial cleaning products, agricultural chemicals such as spray adjuvants, oilfield applications, and various coating additives. Short for surface active agent, a surfactant consists of a hydrophilic moiety, which attracts water, and a hydrophobic moiety, which attracts oil and dirt. The amphiphilic structure of surfactant molecules enables them to suspend dirt, emulsify, and modify surface properties of materials. Variations in the chemical structure of a surfactant molecule can enable tunable properties, such as emulsifying capability (hydrophilic/lipophilic balance), oil/dirt suspension capacity (critical micelle concentration), cold water performance (Krafft point), foaming, and biodegradation.

Surfactants have generally been synthesized from petrochemical feedstocks, such as long chain alkanes/alkenes and ethylene oxide. However, surfactants synthesized from petrochemical feedstocks can present a number of issues. For one, such surfactants include chemicals that can be harmful to the environment. Moreover, such surfactants may not perform as intended in certain applications. For example, despite decades of development, these various surfactant structures are faced by a unified problem—the presence of hard water (e.g., containing calcium, magnesium, iron, etc.) inactivates these surfactants. When inactivation occurs, this causes surfactants to form solid precipitates and substantially lose the intended functionality.

To address some of the issues associated with surfactants synthesized from petrochemical feedstocks, surfactants are beginning to be derived from natural sources, such as oils and sugars. The development has mainly focused on replacing the petrochemical surfactants with bio-based analogues having identical chemical structure. The result is a surfactant that is more eco-friendly relative to petrochemical surfactants.

However, current production of both petrochemical surfactants and the more recently developed bio-based analogues generally involves high-volume production of sodium lauryl ether sulfate (SLES) surfactants. A production byproduct of SLES surfactants is 1,4-dioxane, the target of a number of recent regulatory developments because, according to the US Environmental Protection Agency, 1,4-dioxane is a likely human carcinogen and does not readily biodegrade. As a result, drain discharge of industrial and consumer products (e.g., detergents, cosmetics, shampoos) can cause 1,4-dioxane to come into contact with the general population through drinking water. Indeed, elevated levels of 1,4-dioxane have been detected in the drinking water across the US, spurring legislation that sets limits on the presence of 1,4-dioxane in consumer products. The limit on 1,4-dioxane is problematic for surfactant producers because leading product brands contain levels of 1,4-dioxane at orders of magnitude above the set limits. Accordingly, affected products will either need to exit the market or comply with the new contaminant limits, meaning producers need to redesign current formulations with dioxane-reduced versions or dioxane-free substitutes. Because suppressing 1,4-dioxane formulation during current manufacturing can be costly and difficult due to limits on available technology, this may not be a cost-effective compliance solution.

To further compound the problems facing current surfactant producers, restrictions are being proposed on ethylene oxide emissions, a chemical building block of SLES, considered to be a carcinogenic gas. Such restrictions targeting ethylene oxide emission reductions from surfactant production facilities would require significant and costly equipment modifications that may restrict production capacity for mainstream products.

SUMMARY

In view of the above described challenges, there is a need to introduce SLES substitutes that are dioxane-free and ethoxylate-free. The embodiments disclosed herein can provide surfactant (e.g., oleo-furan surfactant) compositions free of problematic dioxane and ethoxylate and, thereby, provide an alternative that solves the current challenges associated with SLES and other surfactants on the market. Notably, at the same time, the embodiments disclosed herein can provide these alternative surfactant compositions with similar performance, as compared to SLES surfactants, yet while producing these surfactant compositions from renewable resources.

The present disclosure describes chemical composition embodiments as well as embodiments of methods for synthesizing furan surfactants containing calcium, magnesium, ammonium, and/or lithium cations and one of a number of furan derivatives. The embodiments of methods for synthesizing furan surfactants containing calcium, magnesium, ammonium, and/or lithium cations can include novel chemical reagents and purification procedures to prepare furan surfactants containing calcium, magnesium, ammonium, and/or lithium cations.

The furan surfactant embodiments disclosed herein containing calcium, magnesium, ammonium, and/or lithium cations can provide a number of useful, improved associated characteristics, for instance, as compared to sodium cation surfactants. In particular, the furan (e.g., oleo-furan) surfactant composition embodiments disclosed herein can be useful because these furan surfactant compositions can have distinct physical properties and surfactant characteristics resulting from the calcium, magnesium, ammonium, and/or lithium cations included in the furan (oleo-furan) surfactant composition embodiments. For example, the furan (e.g., oleo-furan) surfactant composition embodiments containing calcium, magnesium, ammonium, and/or lithium cations can provide one or more improved characteristics including solubility, Krafft point, critical micelle concentration, surface tension, fabric wetting kinetics, foam generation and foam stability. Thus, furan (e.g., oleo-furan) surfactant compositions disclosed herein can be tuned in a manner that renders these compositions more useful in a variety of everyday surfactant applications.

Particular embodiments disclosed herein include a class of oleo-furan sulfonate surfactant (OFS) molecules as well as methods for tuning desirable properties, for example foaming and critical micelle concentration. More particularly, embodiments disclosed herein include a sub-group of methyl-substituted oleo-furan surfactants that can have beneficial performance properties (e.g., improved critical micelle concentration). As described herein, certain embodiment can neutralize oleo-furan sulfonate surfactants with cations other than sodium (e.g., neutralizing with a calcium cation), which, as a result, can impart unique foaming properties as well as significant improvements in critical micelle concentration (CMC), surface tension at CMC, wetting behavior (e.g. Drave's wetting time), and function in hard water conditions. Combined, the methyl-substituted and calcium-neutralized oleo-furan sulfonate surfactant embodiments disclosed herein can have unique performance properties that mimic (and in some cases outperform) those properties of ether sulfate surfactants (e.g., SLES) but, notably, without the presence of both 1,4-dioxane byproduct and ethylene oxide subunits, which have otherwise typically been needed to obtain the level of performance that can be provided by the embodiments disclosed herein. Accordingly, surfactant embodiments disclosed herein can have properties similar or superior to the commercial surfactant sodium lauryl ether sulfate, SLES, while avoiding the carcinogenic compound 1,4-dioxane otherwise produced as an unavoidable sodium laureth sulfate byproduct. Thus, the surfactant embodiments disclosed herein can provide high-performance, bio-renewable, and dioxane-free alternatives to SLES surfactants.

Typically, anionic surfactants have been neutralized using basic sodium salts since this can provide intended functionality along with acceptable solubility of sodium surfactants in water-based applications. For instance, sodium dodecyl sulfate and sodium dodecylbenzene sulfonate, two common anionic surfactants used in cleaning products, have solubilities of 0.2 and 0.25 g/mL, respectively. In contrast, while calcium forms of these surfactants provide some advantageous characteristics compared to the sodium forms, they have much lower solubility in water, making use in water-based applications more difficult. While direct measures of calcium surfactant solubility can be difficult due to extremely low solubility, Krafft point of calcium dodecyl sulfate can be approximately 29° C., and the solubility of calcium dodecylbenzene sulfonate even at the elevated temperature of 50° C. is estimated to be less than 0.01 g/mL, indicating both calcium surfactants have negligible solubility in room temperature and even slightly elevated temperature solutions. Notably, embodiments disclosed herein, such as the calcium form surfactant seen in Structure A of General Structure 1 below, shows improvement over the sodium form in useful surfactant characteristics as seen in Table 2 below, while at the same time maintaining a solubility higher than the common sodium surfactants noted above (e.g., 0.35 g/mL). This resulting benefit in application can be three-fold: the calcium form surfactant embodiments may not be inactivated by calcium (e.g., from hard water) like common sodium surfactants, the calcium form surfactant embodiments can perform with the functional improvements bestowed by $Ca^{2+}$ cation, and the calcium form surfactant embodiments can still be formulated at a higher concentration than the most common sodium surfactants due to higher solubility.

Another advantage of surfactant embodiments disclosed herein is their inherent stability, particularly in the acid form prior to neutralization (oleo-furan sulfonic acids). As noted elsewhere herein, structural stability is an issue in the production of the common anionic surfactant SLES, causing occasional ring closure of the labile ethoxy chain during ethoxylation and sulfation step, which leads to the formation of a carcinogenic byproduct (e.g., 1,4-dioxane). In contrast, oleo-furan sulfonic acids have shown negligible degradation or byproduct formation by high purity liquid chromatography over an 8-week time course study, both at room temperature and elevated temperature (42° C.).

Critical micelle concentration is a fundamental surfactant characteristic and consistently has economic implications as it impacts the amount of surfactant required to impart a desired effect in application. Embodiments disclosed herein include a structural modification which includes a short alkyl chain on the furan ring and a resulting change in sulfonation position on the furan ring. This change in structure, along with the corresponding changes in surfactant properties, can be seen in Table 3 below. In particular, for the two surfactant structure embodiments listed with and without the methyl group, the presence of a methyl group and shift in sulfonation position can cause a decrease in critical micelle concentration by 34% or 15%, depending on the exact structure of the hydrophilic head group. In certain applications, this could result in a decrease in surfactant loading by the same percentage, making addition of a short alkyl chain on the furan ring a significant cost benefit and improvement on prior structures.

In general, various exemplary embodiments disclosed herein include a method for neutralizing a surfactant. In one example, the surfactant can be a protic monoanionic or diprotic dianionic surfactant. In this method embodiment, a salt containing a cation including at least one of calcium carbonate, or a mixture of basic metal salts, including but not limited to a calcium carbonate and sodium carbonate mixture, is added to a surfactant solution composed of a water and organic solvent mixture, with a ratio of 0-50% organic solvent by volume, where the organic solvent includes acetonitrile. The result is the surfactant salt with the selected cation in solution, which is then reduced to a solid by heating in a temperature range from 25-80° C. while optionally applying vacuum in the pressure range of 0.001-0.99 atm. Removal of residual sulfate or carbonate salts in the product mixture, which may be present in varying quantities depending on the sulfonation conditions and neutralization base salt selected, can be achieved by dissolving the solids in water and adding sufficient organic solvent, including but not limited to acetone, to prepare a 1:1 aqueous to organic solvent solution by volume. This solution can be mixed then stored at a temperature between 0 and 15° C. for a period of time from 1-48 hours. The solid salt can then removed by filtration, and the liquid is removed by heating in a temperature range from 25-80° C. while optionally applying a vacuum in the pressure range of 0.001-0.99 atm. If unsulfonated organics or sulfated byproducts remain in the product mixture, removal can be achieved by recrystallization in organic solvent including but not limited to isopropanol, ethanol, methanol, acetonitrile, acetone, or mixtures including, but not limited to, the aforementioned solvents.

One exemplary embodiment includes a compound having the formula (1):

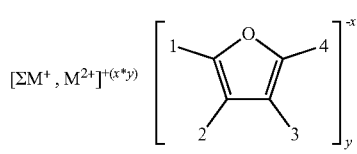

(1)

In embodiments of the formula (1), each numbered position (1-4) designates a functional group, such as —H, —CH$_3$, —CH$_2$CH$_3$, a longer alkyl chain of C$_4$ to C$_{28}$ chain length which may or may not contain a ketone functional group, and —SO$_3$; this structure must contain, at minimum, one longer alkyl chain C$_4$ to C$_{28}$ chain length containing a ketone functional group, and one —SO$_3$ functional group. A complete list of possible substituents for formula (1) are included in Table 1 below. Formula (1) may contain one or more alkylfuran sulfonates, one or more alkylfuran disulfonates, or any combination of the two; these anions may be balanced in charge with one or more monovalent cations including Na$^+$ or NH$_4^+$, one or more divalent cations including Mg$^{2+}$ or Ca$^{2+}$, or any combination of the monovalent and divalent cations described herein. While preferred iterations of formula (1) include one monoanionic oleo-furan sulfonate anion per monovalent cation or two monoanionic oleo-furan sulfonate anions or one dianionic oleo-furan disulfonate per divalent cation, some iterations may not adhere to this ratio, particularly in iterations where mixed cation basic salts are used for neutralization.

Another exemplary embodiment includes a compound having the formula (2):

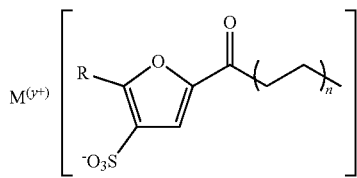

(2)

For the compound having the formula (2) above, M can be selected from the group consisting of: NH$_4^+$, Li$^+$, Ca$^{2+}$, Na$^+$, and Mg$^{2+}$; R can be selected from the group consisting of: CH$_3$ and other alkyl substituents; y can be selected from the group consisting of: 1, 2, and non-integer values between 1 and 2; and n can be an alkyl chain from 4 to 28 carbon atoms in length.

In a further embodiment of the compound having the formula (2), the alkyl chain can include a ketone functional group alpha to the furan ring. In a further embodiment of the compound having the formula (2), R can be CH$_3$. In a further embodiment of the compound having the formula (2), M can be Na$^+$ and y can be 1. In a further embodiment of the compound having the formula (2), M can be NH$_4^+$ and y can be 1. In a further embodiment of the compound having the formula (2), M can be Li$^+$ and y can be 1. In a further embodiment of the compound having the formula (2), M can be Ca$^{2+}$ and y can be 2. In a further embodiment of the compound having the formula (2), M can be Mg$^{2+}$ and y can be 2. In a further embodiment of the compound having the formula (2), M can be a mixture of Na$^+$ and Ca$^{2+}$, and y can be a non-integer value between 1 and 2. In a further embodiment of the compound having the formula (2), M can be a mixture of Na$^+$ and Li$^+$, and y can be 1. In a further embodiment of the compound having the formula (2), M can be a mixture of Na$^+$ and NH$_4^+$, and y can be 1. In a further embodiment of the compound having the formula (2), M can be a mixture of Na$^+$ and Mg$^{2+}$ and y can be a non-integer value between 1 and 2. In a further embodiment of the compound having the formula (2), n can be 4, with 10 total carbon atoms in the alkyl chain. In a further embodiment of the compound having the formula (2), n can be 5, with 12 total carbon atoms in the alkyl chain.

In one embodiment, the compound having the formula (2) can be as follows:

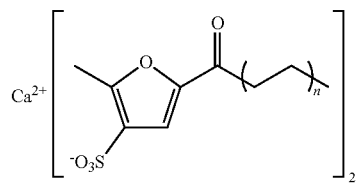

A further specific embodiment of the immediately above compound embodiment of the formula (2) can be as follows:

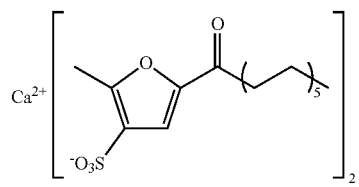

In another embodiment, the compound having the formula (2) can be as follows:

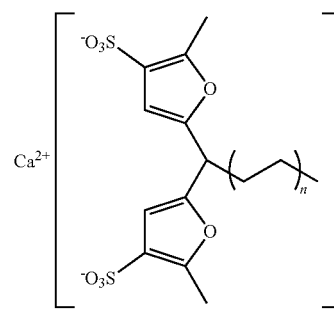

As one example, a further specific embodiment of the immediately above compound embodiment of the formula (2) can include n equal to 5.

In still a further embodiment, the compound having the formula (1) is as follows:

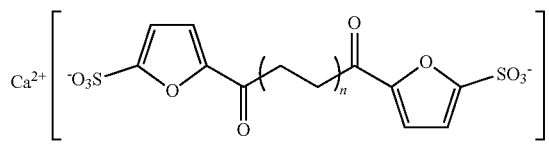

As one example, a further specific embodiment of the immediately above compound embodiment of the formula (2) can include n equal to 4.

One exemplary embodiment of neutralization of an acidic oleo-furan sulfonate (OFS) molecule with Ca, Mg or NH₄ cation base, such as CaCO₃, to form a Ca, Mg or NH₄ salt of the formula (1) is Scheme 1 shown as follows:

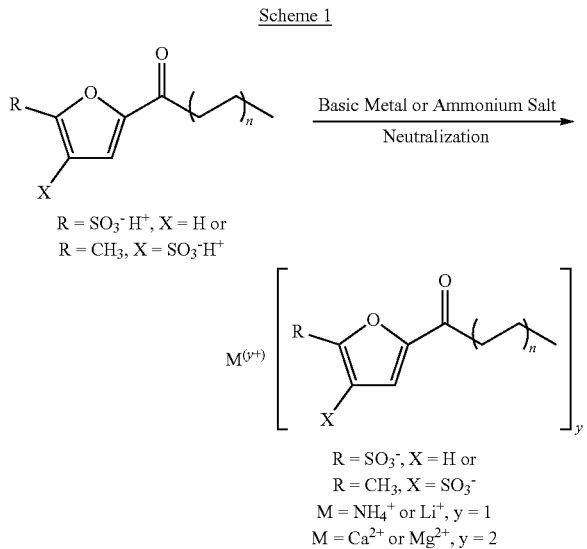

Scheme 1

R = SO₃⁻H⁺, X = H or
R = CH₃, X = SO₃⁻H⁺

R = SO₃⁻, X = H or
R = CH₃, X = SO₃⁻
M = NH₄⁺ or Li⁺, y = 1
M = Ca²⁺ or Mg²⁺, y = 2

BRIEF DESCRIPTION OF THE DRAWING

FIG. 1 shows an example plot of stability tracking for oleo-furan sulfonic acid surfactant precursor.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of elements, materials, compositions, and/or steps are provided below. Though those skilled in the art will recognize that many of the noted examples have a variety of suitable alternatives that are also within the scope of the present disclosure.

Embodiments described herein relate to surfactant compositions and related methods for synthesizing such surfactants. In particular, disclosed herein are embodiments including surfactant compositions free of dioxane and ethoxylate, produced from renewable sources, while providing similar performance as compared to SLES surfactants.

Sulfonation and sulfation reactions generally are the final process step in commercial surfactant manufacturing. Alkylfuran sulfonates, alkyldifuran sulfonates, and SLES are the product of sulfonation and sulfation reactions. From a chemical perspective, sulfonation describes the reaction of an organic surfactant precursor, such as alkyl benzene or the oleo-furan surfactant embodiments disclosed herein, with sulfur trioxide (SO₃) to form a stable sulfur-carbon bond in the acid surfactant product (alkyl benzene sulfonic acid, embodiments of oleo-furan sulfonic acid disclosed herein). Due to the stability of the sulfur-carbon-bond, sulfonic acids can generally be isolated, stored, and shipped in their pure acid form. Sulfations, on the other hand, involve the reaction between an organic alcohol surfactant precursor, such as ethoxylated lauryl alcohol, and SO₃ to form a hydrolytically instable carbon-oxygen-sulfur bond in the surfactant product (SLES). In order to avoid rapid decomposition of this unstable acid form, immediate neutralization and dilution of the sulfated product can be needed, resulting in high shipping costs for the dilute surfactant solution (30-70% active surfactant). Accordingly, one useful advantage of oleo-furan surfactant embodiments disclosed herein can be sulfonates and would thus be able to provide a stable concentrated acid form, leading to reduced shipping expenses and the possibility of on-site custom-neutralization by surfactant customers.

Commercially, there are multiple techniques for the production of detergent range sulfonates and sulfates. For all of them, major challenges are heat removal and control of the molar SO₃ to organic precursor ratio, two process factors that are dictating the extent of side reactions and amount of byproducts formed due to the highly exothermic character of the reaction. In the past, this challenge has been tackled by using dilute or complexed SO₃ precursors, reducing the rate of sulfonation or sulfation.

The following types of diluting/complexing SO₃ reagents are commercially used (with an increase in usage in the order as they appear): sulfamic acid<chlorosulfuric acid<oleum<air/SO₃. Sulfamic acid is used to sulfate alcohols and ethoxylated alcohols, such as SLES, and directly forms the ammonium neutralized salt. It is one of the mildest and most selective sulfating agents that does not react with aromatic rings, such as alkyl benzene or the proposed oleo-furan surfactant, and tends to be economically useful only for small batch processes due to the high cost of the SO₃ precursor salt. Chlorosulfuric acid is also exclusively used to sulfate alcohols and ethoxylated alcohols, and reacts rapidly and stoichiometrically to the sulfated product, which requires immediate neutralization once the reaction is complete. Oleum (SO₃.H₂SO₄), on the other hand, is predominantly used for sulfonations of aromatics, such as alkyl benzene, and can be used for embodiments disclosed herein, and has the advantage of low feedstock and capital equipment cost. The downside to this technique is that oleum-based sulfonation is an equilibrium process leaving large quantities of unreacted sulfuric acid behind that cannot be entirely separated leading to ca. 8% of sodium sulfate in the neutralized product. Lastly, the SO₃/air process is generally used the most and has been steadily replacing the oleum process. The SO₃/air-process is capable of both sulfonating and sulfating a wide range of organic feedstocks. Generally, the process is rapid and stoichiometric, produces high quality product under tight control of reaction conditions, and is best suited for large-scale continuous production. The organic feedstock, such as aromatics, alcohols or ethoxylated alcohols (i.e. SLES), is reacted with a mix of SO₃ gas (typically sourced from sulfur) and very dry air. The resulting sulfonic or sulfuric acid is then combined with neutralizing agent (usually 50% sodium hydroxide), water as diluent and possible additives, producing a solution of neutral active surfactant (a slurry or paste) of the desired composition and pH. While immediate neutralization of SLES is inevitable to prevent decomposition, notably, stability of oleo-furan sulfonic acid could allow to omit neutralization and dilution after SO₃/air sulfonation, resulting in the described benefits of lower shipping costs and on-site neutralization by formulators.

Feedstocks for this process may also include solvents or any other residual reagents or byproducts from the surfactant sulfonation process, as the neutralization may be applied directly to the sulfonation effluent stream. Preferably, the feedstock stream will contain only acid form oleo-furan sulfonates in the absence of solvent (neat). 1351 Feedstocks used in the process can include but are not limited to alkylfuran sulfonates and alkyldifuran sulfonates with carbon chain lengths varying from ($C_4$ to $C_{28}$) that can be saturated or unsaturated (mono-, di-, or tri-). The alkylfuran sulfonate structure in the feedstocks may include, in part, a furan moiety or furan derivatives such as methylfuran, ethylfuran, or furfural. 1361 The following provides a general description of an embodiment of an exemplary neutralization procedure. In general, neutralization of protic monoanionic or diprotic dianionic surfactant is achieved by addition (e.g., relatively slow addition) of a basic salt containing the cation of choice, including but not limited to calcium carbonate, or a mixture of basic metal salts, including but not limited to a calcium carbonate and sodium carbonate mixture, to a surfactant solution composed of a water and organic solvent mixture, wherein the ratio is 0-50% organic solvent by volume, and the organic solvent includes, but is not limited to acetonitrile. This process results in the surfactant salt with the selected cation in solution, which is then reduced to a solid by heating in a temperature range from 25-80° C. while optionally applying vacuum in the pressure range of 0.001-0.99 atm. Removal of residual sulfate or carbonate salts in the product mixture, which may be present in varying quantities depending on the sulfonation conditions and neutralization base salt selected, can be achieved by dissolving the solids in a minimum of water and adding sufficient organic solvent, including but not limited to acetone, to prepare a 1:1 aqueous to organic solvent solution by volume. This solution is mixed thoroughly, then stored at a temperature between 0 and 15° C. for a period of time from 1-48 hours. The solid salt is then removed by filtration, and the liquid is removed by heating in a temperature range from 25-80° C. while optionally applying a vacuum in the pressure range of 0.001-0.99 atm. If unsulfonated organics or sulfated byproducts remain in the product mixture, removal can be achieved by recrystallization in organic solvent including but not limited to isopropanol, ethanol, methanol, acetonitrile, acetone, or mixtures composed of, but not limited to, the aforementioned solvents.

One exemplary embodiment of a neutralization process is depicted below as Scheme 1, and one exemplary embodiment of a composition formed from Scheme 1 is depicted below as General Structure 1.

Scheme 1

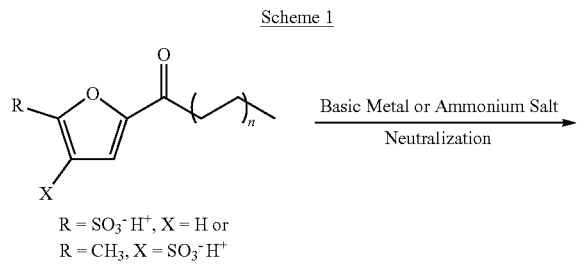

$R = SO_3^- H^+, X = H$ or
$R = CH_3, X = SO_3^- H^+$

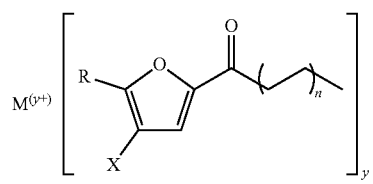

$R = SO_3^-, X = H$ or
$R = CH_3, X = SO_3^-$
$M = NH_4^+$ or $Li^+$, $y = 1$
$M = Ca^{2+}$ or $Mg^{2+}$, $y = 2$

General Structure 1

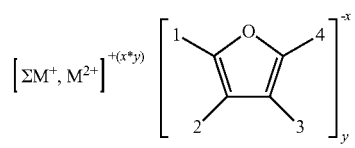

Scheme 1 illustrates an exemplary neutralization of an acidic oleo-furan sulfonate (OFS) molecule with Ca, Mg, $NH_4$, or Li cation base, such as $CaCO_3$, to form a Ca, Mg, $NH_4$, or Li salt of the General Structure 1, where each numbered position (1-4) designates a functional group, such as —H, —$CH_3$, —$CH_2CH_3$, a longer alkyl chain of $C_4$ to $C_{28}$ chain length which may or may not contain a ketone functional group, and —$SO_3$; this structure contains, at minimum, one longer alkyl chain $C_4$ to $C_{28}$ chain length containing a ketone functional group, and one —$SO_3$ functional group. A complete list of possible substituents for General Structure 1 is included in Table 1 below. General Structure 1 may contain one or more alkylfuran sulfonates, one or more alkylfuran disulfonates, or any combination of the two; these anions may be balanced in charge with one or more monovalent cations including $Na^+$, $NH_4+$, or $Li^+$, one or more divalent cations including $Mg^{2+}$ or $Ca^{2+}$, or any combination of the aforementioned monovalent and divalent cations. While preferred iterations of General Structure 1 will contain one monoanionic oleo-furan sulfonate anion per monovalent cation or two monoanionic oleo-furan sulfonate anions or one dianionic oleo-furan disulfonate per divalent cation, some iterations may not adhere to this ratio, particularly in iterations where mixed cation basic salts are used for neutralization. 1391 Table 1 lists examples of substituents of the furan-based surfactant of General Structure 1.

TABLE 1

Furan Substituents (GS1)

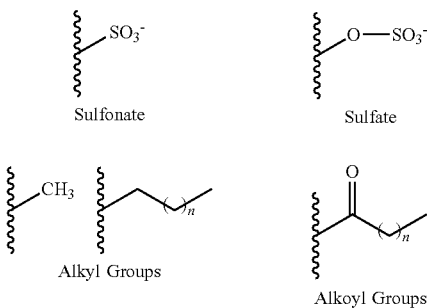

TABLE 1-continued

Furan Substituents (GS1)

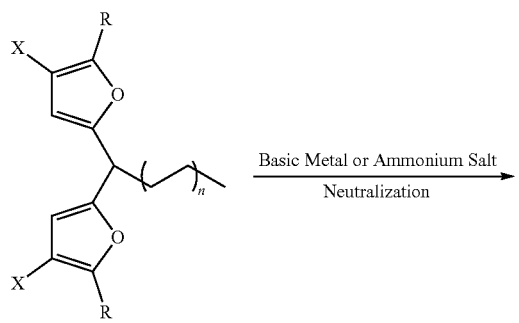

Alkylfuran Sulfonate Groups

Alkoylfuran Sulfonate Groups

Table 1

The following describes preparation of dianionic calcium, magnesium, ammonium, and lithium surfactants of General Structure 1 are seen below and can be prepared from the corresponding acid forms according to Schemes 2 and 3, respectively.

One exemplary embodiment of preparing calcium, magnesium, ammonium, and lithium cation dianionic oleo-furan surfactants with a tailed alkyl chain is depicted below as Scheme 2.

Scheme 2

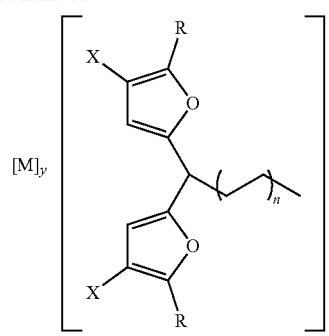

R = $SO_3^-$ $H^+$, X = H or
R = $CH_3$, X = $SO_3$-$H^+$

M = $NH_4^+$ or $Li^+$, y = 2
M = $Ca^{2+}$ or $Mg^{2+}$, y = 1

One exemplary embodiment of preparing calcium, magnesium, ammonium, and lithium cation dianionic oleo-furan surfactants with a bridging alkyl chain is depicted below as Scheme 3.

Scheme 3

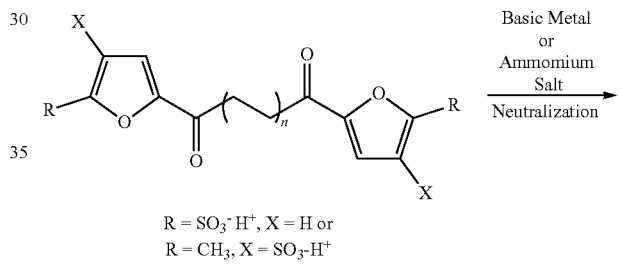

R = $SO_3^-$ $H^+$, X = H or
R = $CH_3$, X = $SO_3$-$H^+$

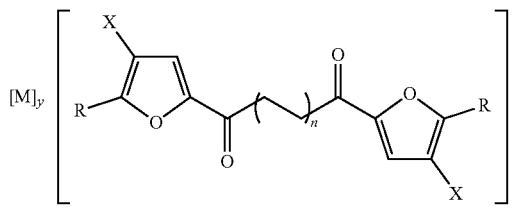

R = $SO_3^-$ $H^+$, X = H or
R = $CH_3$, X = $SO_3^-$
M = $NH_4^+$ or $Li^+$, y = 2
M = $Ca^{2+}$ or $Mg^{2+}$, y = 1

In further embodiments of the above depicted Scheme 1, Scheme 2, and Scheme 3, a basic calcium salt, such as calcium hydroxide, can be used to neutralize the acid form surfactants.

One exemplary embodiment using a basic salt to neutralize the acid form surfactant of Scheme 1 is depicted below as Scheme 4.

Scheme 4

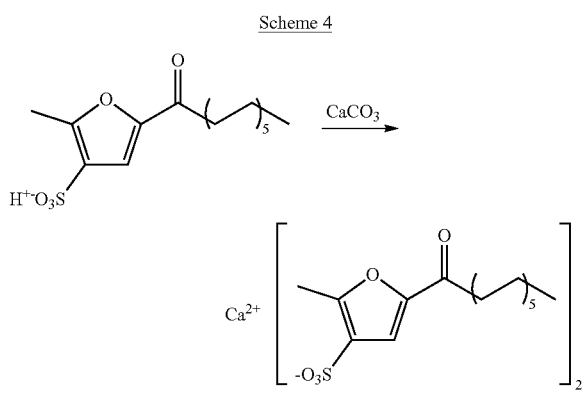

Scheme 4 shows surfactant preparation from a protic monoanionic oleo-furan sulfonate containing a tailed alkyl chain. The structure shown in Scheme 4 has a $C_{12}$ alkoyl saturated carbon chain derived from lauric acid. Alternately, surfactants can also be derived from a distribution of fatty acids with varying alkyl chain length, and varying degrees of unsaturation can be used, such as those obtained from soybean oil, to produce surfactant mixtures of varying alkyl chain length, the final product of which may or may not contain chain unsaturation.

One exemplary embodiment using a basic salt to neutralize the acid form surfactant of Scheme 2 is depicted below as Scheme 5.

Scheme 5

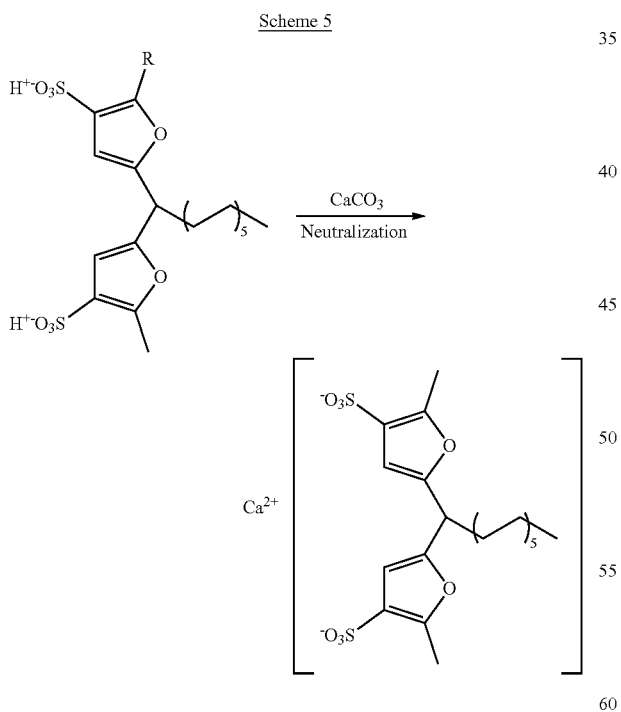

Scheme 5 shows surfactant preparation from a protic dianionic oleo-furan sulfonate containing a tailed alkyl chain.

One exemplary embodiment using a basic salt to neutralize the acid form surfactant of Scheme 3 is depicted below as Scheme 6.

Scheme 6

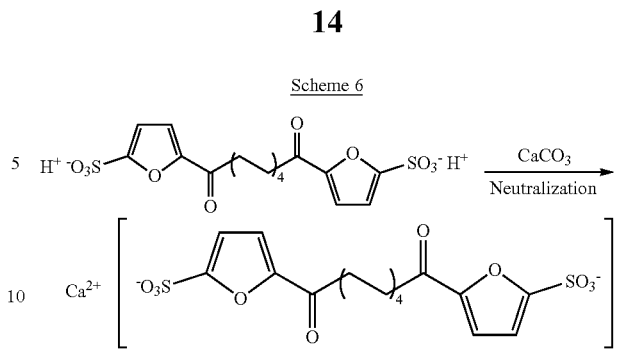

Scheme 6 shows surfactant preparation from a protic dianionic oleo-furan sulfonate containing a bridging alkyl chain.

The following describes embodiments of surfactant structures, for instance that can result from process embodiments (e.g., neutralization scheme embodiments) described herein. The surfactant structure embodiments described as follows are based on General Structure 1, provided above. These surfactant structure embodiments can be part of a class of calcium, magnesium, ammonium, and lithium cation oleo-furan surfactant, for example with either one or two furan moieties acting as part of a hydrophilic head, and the hydrophobic alkyl chain as either a bridging or terminal carbon chain.

In each of these further surfactant structure embodiments based on General Structure 1, the alkyl chain length either on the terminal end of the furan moiety (e.g., as seen in Structures A and B of General Structure 1) or between furan molecules (e.g., as seen in Structure C of General Structure 1) can vary, for example, from $C_4$ to $C_{28}$ or in the alkyl chain range of $C_4$ to $C_{18}$ or in the alkyl chain range of $C_6$ to $C_{18}$ or in the alkyl chain range $C_8$ to $C_{14}$. The length of the alkyl chain can be an important surfactant structural feature and can significantly alter surfactant characteristics, including factors that impact performance in applications, such as laundry detergency. For these reasons, alkyl chain lengths in one range, e.g. $C_1$-$C_3$, are considered to produce surfactants with significantly different application performance than those in another range, e.g. $C_4$-$C_{28}$.

Referring back to General Structure 1, functional groups designated by number positions (1-4) can be —H, —CH$_3$, —CH$_2$CH$_3$, a longer alkyl chain, —OH, polyglycoside, polyethoxylate, sulfate, sulfonate, or any of the other functional groups listed in Table 1 above.

One embodiment of a surfactant structure based on General Structure 1 is depicted below as Structure A of General Structure 1.

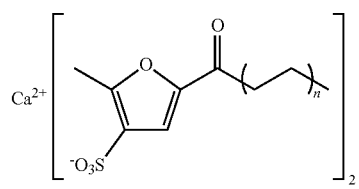

Structure A of General Structure 1

Another embodiment of a surfactant structure based on General Structure 1 is depicted below as Structure B of General Structure 1.

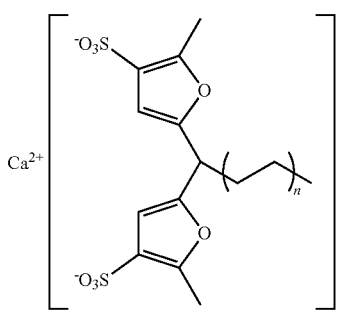

Structure B of General Structure 1

A further embodiment of a surfactant structure based on General Structure 1 is depicted below as Structure C of General Structure 1.

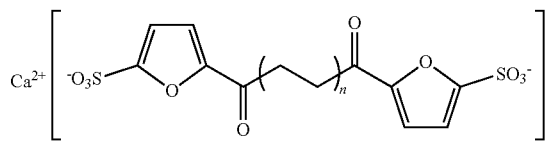

Structure C of General Structure 1

Example

The following provides illustrative, non-limiting experimental examples of methods of synthesis and related synthesized structures.

A monoanionic oleo-furan surfactant according to Structure A of General Structure 1 was prepared from the corresponding oleo-furan sulfonic acid as outlined in Scheme 4, and this calcium oleo-furan surfactant is shown below as Experimental Structure 1.

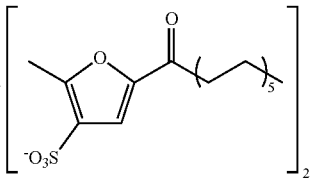

Experimental Structure 1

Referring to Experimental Structure 1, neutralization of the oleo-furan sulfonic acid was performed by dissolving the acid in a 1:1 solution (v/v) of water and acetonitrile, followed by addition of calcium carbonate (>99%, Sigma), prompting release of $CO_2$ gas. Addition of the calcium salt was continued until gas formation ceased and insoluble salt was observed. The pH of the solution was measured, and the mixture was allowed to stir until the pH was at least 6, or for approximately 12 hours. The mixture was then filtered to remove excess carbonate salt, and reduced to a solid on a hot plate at 50° C. Further salt removal was achieved by dissolving in a 1:1 solution of water and acetone, chilling for 4 hours at 4° C., and filtering. After drying the filtrate to a solid by hot plate at 50° C., recrystallization in a 1:1 solution of isopropanol and acetone yielded the off-white solid product.

The following Table 2 provides selected surfactant physical characteristics and performance metrics relative to SLES.

TABLE 2

| Cation | CMC[1] (ppm) | Surface Tension[2] (mN/m) | Ross Miles Foam Height[3] (mm) | High Shear Foam Height[4] (mm) | High Shear Foam Loss[5] (%) | Calcium Tolerance[6] (ppm) | Wetting Time[7] (sec) | Solubility[8] (g/mL) | Krafft Point (° C.) |
|---|---|---|---|---|---|---|---|---|---|
| $Na^+$ | 1480 | 42 | 134/132 | 71/69 | 30 | >50,000 | 45 | 0.8 | <0 |
| $Ca^{2+}$ | 300 | 33 | 180/170 | 53/51 | 11 | >50,000 | 25 | 0.35 | <0 |
| $Mg^{2+}$ | — | 38* | 185/175 | 43/41 | 16 | >50,000 | 22 | 0.01 | 20 |
| $Li^+$ | 1347 | 45 | 135/120 | 85/84 | 28 | >50,000 | 27 | 0.3 | <0 |
| $NH_4^+$ | 3309 | 39 | 75/55 | 23/8 | 0 | >50,000 | >300 | 1 | <0 |
| SLES[†] | 449 | 32 | 160/150 | 50/48 | 42 | >50,000 | 14 | ≥1 | <0 |

[1]Critical micelle concentration
[2]Surface tension at critical micelle concentration
[3]Height of foam immediately after foam formation and after 5 minutes, performed according to ASTM D1173
[4]Height of foam in distilled water solution immediately after foam formation and after 5 minutes, performed according to ASTM D319-88 with a blend rate of 13,700 rpm and concentration of 0.1 wt % surfactant
[5]Percent of high shear foam height lost when identical test is run in a 100 ppm hard water solution
[6]Expressed as ppm of $Ca^{2+}$ from a $CaCl_2$ source salt at the concentration where sustained precipitate is noted
[7]Wetting of cotton skein at 30° C. (Testfabrics) according to ASTM D2281
[8]Solubility in deionized water at 20° C.
[9]Foam height increased with the addition of hard water
*Recorded for saturated surfactant solution at 20° C.
[†]Sodium laureth sulfate surfactant with 3 ethoxylates (Stepan STEOL CS 330) used as comparison Synthesized surfactants including the structure depicted in Experimental Structure 1, as well as the corresponding Na, Li, $NH_4$, and Mg surfactants, were tested to determine surfactant properties. These included the time required for the surfactant solution to wet cotton fabric, the amount of foam the surfactant generates when agitated, the tolerance of the surfactant to calcium ions in solution as a measure of surfactant performance in hard water, and the temperature below which the surfactant forms a solid precipitate, known as the Krafft Point.

The results are listed in Table 2, above. These results show significant differences in performance as a function of cation. In particular, superior surface tension, critical micelle concentration, and wetting kinetics were observed with the calcium cation surfactants compared to sodium surfactants prepared in previous technology. The calcium and magnesium monoanionic surfactants were both observed to have high foaming and foam stability, which is attractive for a number of applications including home cleaning, personal care, detergents, cosmetics, ore floatation and oil recovery. In comparison to the common industrial surfactant SLES, which is known for its wide use across numerous home and personal care products despite the carcinogenic byproduct 1,4-dioxane, the calcium surfactant had very similar performance metrics, and even showed improvements in critical micelle concentration, foaming, and high shear foam stability in hard water. Stability of the oleo-furan surfactant, specifically the acid form oleo-furan sulfonic acid that is a precursor to the calcium and other cation surfactants, was measured over an eight week time course at room temperature and elevated temperatures, the results of which can be seen in FIG. 1. FIG. 1 shows stability tracking for oleo-furan sulfonic acid surfactant precursor.

In addition to having a unique cation from previous oleo-furan surfactants, the compositions disclosed herein can contain an additional short alkyl chain on the furan ring. While this change in structure can be minimal, the impact on resulting surfactant characteristics is substantial and would not have been predictable.

Table 3 depicted below shows selected surfactant physical characteristics and performance metrics for varying surfactant structures.

TABLE 3

| Hydrophilic Head Group Structure | CMC[1] (ppm) | Surface Tension[2] (mN/m) | Ross Miles Foam Height[3] (mm) | High Shear Foam Height (mm) | High Shear Foam Loss (%) | $Ca^{2+}$ Tolerance[4] (ppm) | Wetting Time[5] (sec) | Krafft Point (° C.) |
|---|---|---|---|---|---|---|---|---|
| 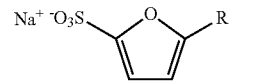 | 1470 | 31 | 151/138 | 36/34 | 22 | 1,000 | 8 | 29 |
| 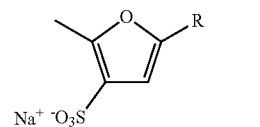 | 968* | 37* | 160/153 | ‡ | ‡ | <100† | 7† | 48 |
| 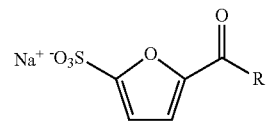 | 1735 | 44 | 138/112 | 70/65 | 0[6] | >50,000 | 34 | <0 |
| 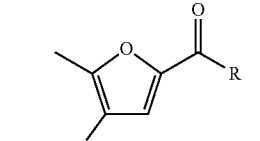 | 1480 | 42 | 134/132 | 70/65 | 17 | >50,000 | 45 | <0 |

'R' designates the position at which the hydrophlic head group is connected to a long alkyl chain. All compounds compared here have alkyl chains of identical length.

[1]Critical micelle concentration

[2]Surface tension at critical micelle concentration

[3]Height of foam immediately after foam formation and after 5 minutes, performed according to ASTM D1173

[4]Expressed as ppm of $Ca^{2+}$ from a $CaCl_2$ source salt at the concentration where sustained precipitate is noted

[5]Wetting of cotton skein at 30° C. (Testfabrics) according to ASTM D2281

[6]Foam height increased with the addition of hard water

*Recorded for saturated surfactant solution at 20° C.

†Performed at 48° C. to allow for sufficient dissolved solid with high Krafft point ‡Experiment could not be performed due to the surfactant's high Krafft point (low solubility)

As can be seen in Table 3, addition of a methyl short alkyl chain to the surfactant head group results in a change of sulfonation position from directly adjacent to the furan oxygen atom. This change in structure had been observed to elicit a significant decrease in critical micelle concentration. In addition, changes in surface tension, foam height, foam stability, calcium tolerance, wetting time and Krafft point were observed; in effect, every surfactant characteristic measured was altered due to the presence of a short alkyl chain on the furan ring. As these surfactant characteristics are useful to performance in application, this modification to the surfactant structure is highly relevant to use in everyday applications.

Table 4 shows the time taken to separate an emulsion comprised of an equal volume 0.1 wt % surfactant solution and soybean oil. The length of time a surfactant solution can maintain an oil-water emulsion is relevant to any application in cleaning, including in detergency, personal care, and industrial cleaning products, as well as for oilfield applications. As was seen for other surfactant properties, emulsion stability was seen to change significantly (18% increase) with the addition of a methyl group on the furan ring. The cation selection was also observed impact emulsion stability, with the calcium form of the methylfuran surfactant (OMFS-12-1/0) maintaining an emulsion nearly 5 times longer than the sodium form.

TABLE 4

| Surfactant | Average Emulsion Separation Time, 15 mL * (min) |
|---|---|
| Na⁺ ⁻O₃S-furan-C(O)-R, Na⁺ OFS-12-1/0 (R = C₁₁H₂₃) | 3.6 |
| methyl-furan-SO₃⁻Na⁺ -C(O)-R, Na⁺ OMFS-12-1/0 (R = C₁₁H₂₃) | 4.4 |
| Li⁺ OMFS-12-1/0 | 3.7 |
| NH⁺₄ OMFS-12-1/0 | 6.1 |
| Ca²⁺ (OMFS-12-1/0)₂ | >20 |

*Separation time indicates the time taken for the surfactant-oil emulsion to separate and reach the specified volume. Surfactant concentration is 0.1 wt %, mixture is 20 mL each of surfactant solution and soybean oil Table 5 provides a comparison of stain removal performance of a furan surfactant (OFS-12-1/0) vs. the analogous methylfuran surfactant (OMFS-12-1/0) for hard set blood stains on cotton fabric. The stain removal index (SRI) is a measure of the amount of stain removed based on the change in RGB values before and after washing, with a higher SRI indicating more stain removal. When washed with a 0.1 wt % aqueous solution of surfactant, a significant difference in SRI was observed between the furan and methylfuran surfactants, providing further evidence the structure change on the furan moiety results in performance differences that would not be obvious to one skilled in the art.

TABLE 5

| Surfactant | Stain Removal Index: Hard Set Blood on Cotton Fabric[†] |
|---|---|
| Na⁺ ⁻O₃S-furan-C(O)-R, Na⁺ OFS-12-1/0 (R = C₁₁H₂₃) | 20.3 |
| methyl-furan-SO₃⁻Na⁺ -C(O)-R, Na⁺ OMFS-12-1/0 (R = C₁₁H₂₃) | 13.2 |

[†]Wash conditions: stained fabric was purchased from Testfabrics Inc. (Item #2210026) and washed by agitating for 1 minute in a 0.2 L 0.1 wt % surfactant solution at 20° C., then rinsing in deionized water. Stain removal index was calculated by photographing the stained fabric before and after washing with an Olympus E-M10 Mark II camera, then following methods outlined in ASTM D2244.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A compound having the formula (1)

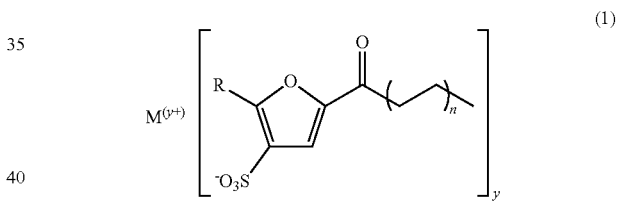

wherein M is selected from the group consisting of: NH₄+, Li⁺, Ca²⁺, Na⁺, and Mg²⁺,
wherein R is selected from the group consisting of: CH₃ and other alkyl substituents,
wherein y is selected from the group consisting of 1, 2, and non-integer values between 1 and 2, and
wherein n is an alkyl chain from 4 to 28 carbon atoms in length.

2. The compound of claim 1, wherein the alkyl chain includes a ketone functional group alpha to the furan ring.

3. The compound of claim 1, wherein R is CH₃.

4. The compound of claim 1, wherein M is Na⁺ and y is 1.

5. The compound of claim 1, wherein M is NH₄⁺ and y is 1.

6. The compound of claim 1, wherein M is Li⁺ and y is 1.

7. The compound of claim 1, wherein M is Ca²⁺ and y is 2.

8. The compound of claim 1, wherein M is Mg²⁺ and y is 2.

9. The compound of claim 1, wherein M is a mixture of Na⁺ and Ca²⁺ and y is a non-integer value between 1 and 2.

10. The compound of claim 1, wherein M is a mixture of Na⁺ and Li⁺ and y is 1.

11. The compound of claim 1, wherein M is a mixture of Na⁺ and NH₄⁺ and y is 1.

12. The compound of claim 1, wherein M is a mixture of Na⁺ and Mg²⁺ and y is a non-integer value between 1 and 2.

13. The compound of claim 1, wherein n is 4, with 10 total carbon atoms in the alkyl chain.

14. The compound of claim 1, wherein n is 5, with 12 total carbon atoms in the alkyl chain.

15. The compound of claim 1, wherein the compound is:

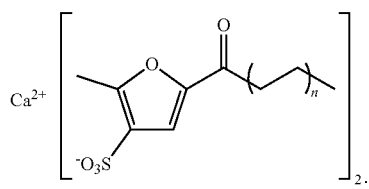

16. The compound of claim 15, wherein the compound is:

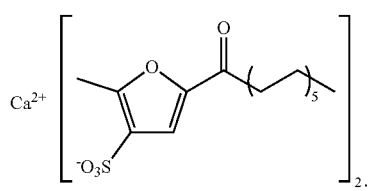

17. The compound of claim 1, wherein the compound is:

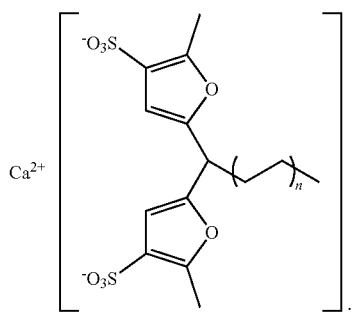

18. The compound of claim 17, wherein n is 5.

19. The compound of claim 1, wherein the compound is:

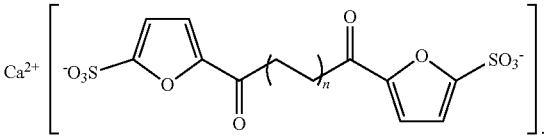

20. The compound of claim 19, wherein n is 4.

* * * * *